March 11, 1975 B. L. COBIA Plant Pat. 3,690

CACTACEAE PLANT

Filed Jan. 25, 1974

United States Patent

Plant Pat. 3,690

Patented Mar. 11, 1975

1

3,690

CACTACEAE PLANT

Barnell L. Cobia, Winter Garden, Fla., assignor to B. L. Cobia, Inc., Winter Garden, Fla.

Filed Jan. 25, 1974, Ser. No. 436,441

Int. Cl. A01h 5/00

U.S. Cl. Plt.—88 1 Claim

ABSTRACT OF THE DISCLOSURE

A new and distinct hybrid plant variety of the Cactaceae family is principally distinguished by a growth habit which in comparison to the "Christmas Cheer" variety combines the following characteristics: A faster growth rate, substantially greater resistance to flower bud abscission, broader, longer and thicker cladophylls, a more upright and compact appearance, greater resistance to nutrient deficiencies and fungus diseases, and a flower with a bloom life from about six to about eight days and perianth tube laminating and forming tepals with marginal blade areas that in color are dominated by purplish pink, reddish purple and/or purplish red hues.

Figure 1:
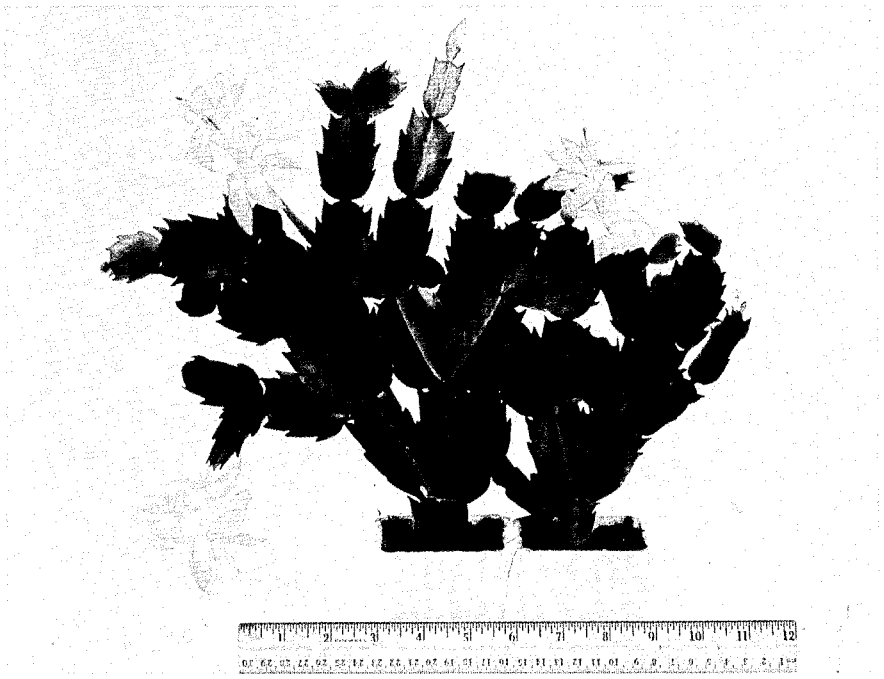

The invention relates to a new and distinct plant variety of the Cactaceae family and which has been named the *Zygocactus truncatus* "Lavender Doll" by the inventor.

Certain plant varieties of the Cactaceae family are well known in the foliage plant market and among these are those of the *Zygocactus truncatus* variety commonly known as the "Christmas Cheer" variety. A lesser known variety that has appeared in the foliage plant market is the *Zygocactus truncatus* "Violacea." These varieties tend to bloom in the months of November and December in the northern hemisphere and hence their appearance in the retail market area is primarily during the Thanksgiving and Christmas seasons.

The "Violacea" variety has what may be called a "purplish" colored bloom that is appealing to purchasers during the Thangsgiving-Christmas holiday season. The bloom life however varies from about 3 to about 6 days and this provides a tolerable shelf life to some merchants at the retail level of sales while others find the bloom life to be unacceptable. The variety suffers from the further disadvantage that many of the flower buds which start to mature fail to reach maturity and instead drop from the stems. Tests have indicated that this bud abscission problem is aggravated when the plant specimens are housed in closed cartons such as are used for shipping purposes in the industry. Growers are accordingly reluctant to grow the variety because of transportation delays and the large costs that are involved in manually selecting specimens for shipment which are at the proper stage of budding to provide reasonable assurance of mature blooming when the plants reach their destination. The variety is generally considered to be a "slower grower" and it has a low tolerance to nutrient deficiencies and also a resistance to fungus-type diseases which is less than satisfactory to many growers.

The variety commonly known as "Christmas Cheer" has a greater resistance to bud abscission, a greater tolerance to nutrient deficiencies and fungus diseases and a faster growth rate than the "Violacea" variety. It also has a bloom life which is generally acceptable to most retail merchants and which is in the area of from about 5 to 8 days. The bloom has what may be called a "salmon" color however and this color is less appealing to the general public during the Thanksgiving-Christmas season. There is accordingly a need for a *Zygocactus truncatus* variety which blooms in the Thanksgiving-Christmas season and has a "purplish" colored bloom and a bloom life which provides a suitable shelf life at the retail level of sales.

2

A general object of the invention has been to develop a variety of the Cactaceae family which would have a "purplish" colored bloom along with a more acceptable bloom life and resistance to flower bud abscission than the "Violacea" variety. Yet another object of the invention has been to develop a variety having a foregoing general objective and which is faster growing and more compact in appearance than the "Violacea" variety.

The objectives of the invention have been fully realized by the development of the new plant variety hereinafter described in detail. The new plant variety was developed in a nursery located at Winter Garden, Fla., as a hybrid secured by cross-pollinating the flower of a plant specimen of a variety developed by the inventor from a vegetative mutation that appeared on a specimen of the "Christmas Cheer" variety with pollen from a plant specimen of another variety that was also developed by the inventor from a vegetative mutation that appeared on a specimen of the "Christmas Cheer" variety. Both parental varieties are research varieties that have not appeared on the market and each generally has the physical, growth rate, bloom life, toleraance to nutrient deficiencies and fungus diseases and abscission characteristics that are attributatable to plant specimens of the "Christmas Cheer" variety. The maternal variety however has a bloom with light pastel salmon coloring while the paternal variety has a streaked pink colored bloom. The seeds taken from the fertilized seed pod were cultivated at the mentioned nursery location and after prolonged observation of the seedlings, the hybridized plant of the new plant variety was selected and asexually reproduced by the inventor at the Winter Garden nursery by the propagation of the stem cuttings taken from the original hybrid plant.

Through successive propagations, it has been ascertained that plants of the new variety generally resemble the parent and "Christmas Cheer" varieties but are distinguishable from these varieties and from other related varieties known to the inventor by a growth habit which is evident in plant specimen propagated and grown under nursery conditions utilized in the growing of tropical plants at Winter Garden, Fla., as combining the following principal characteristics:

1. A faster growth rate than specimens of the "Christmas Cheer" variety,
2. Substantially greater resistance to flower bud abscission than specimens of the "Christmas Cheer" variety,
3. Broader, longer and thicker cladophylls than specimens of the "Christmas Cheer" variety,
4. A more upright and compact (denser) appearance than specimens of the "Christmas Cheer" variety, as evidenced by more erect stems with heavier (more frequent) branching,
5. Greater resistance to nutrient deficiencies and fungus-type diseases than specimens of the "Christmas Cheer" variety, and
6. A flower which has a bloom life from about 6 to about 8 days and perianth tube laminating and forming tepals with marginal blade areas that in color are dominated by purplish pink, reddish purple, and/or purplish red hues.

Figure 2:
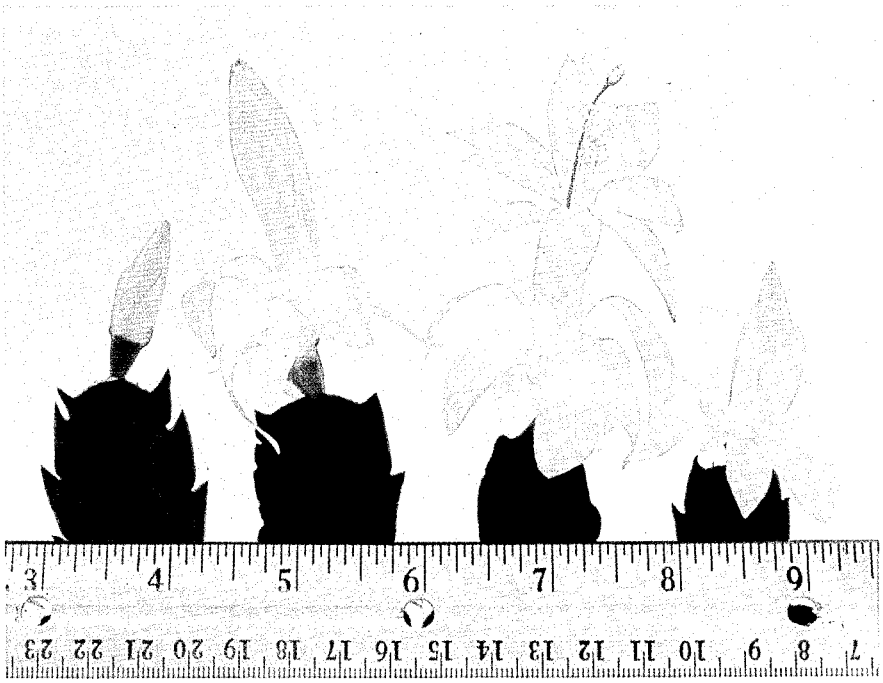

The accompanying drawings serve, by color photographic means, to illustrate the new plant variety and wherein:

FIG. 1 is a color photograph of two potted plant specimens of the new plant variety; and FIG. 2 is a color photograph showing a fully opened bloom of the new variety together with buds of the new variety in earlier stages of bloom maturity.

The following is a detailed description of the new plant variety with colors and hues, unless otherwise clearly indicated by the text through the absence of color notations, being named in accord with the ISCC–NBS Method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The description is further based on observations of well fertilized plants of less than one year of age from initial propagation and which were grown under 50–70% shaded glasshouse nursery conditions in the Winter Garden, Fla. area and wherein temperatures range from 60° to 85° F. during the winter months, from 75° to 95° F. during the summer months and are ambient during intervening periods.

DETAILED PLANT DESCRIPTION

Name: *Zygocactus truncatus* "Lavender Doll."

Parentage:

*A. Paternal.*—Unnamed and unmarketed variety having streaked pink color characteristics in the bloom and developed by the inventor from a vegetative mutation that appeared on a plant specimen of the *Zygocactus truncatus* variety known commercially as "Christmas Cheer."

*B. Maternal.*—Unnamed and unmarketed variety having light pastel salmon color characteristics in the bloom and developed by the inventor from a vegetative mutation that appeared on a plant specimen of the *Zygocactus truncatus* variety known commercially as "Christmas Cheer."

Classification:

*A. Botanic (Britton and Rose, The Cactaceae, Constable and Co., Ltd., London, 1937, Vol. IV).*—(1) Family: Cactaceae. (2) Tribe: Cereeae. (3) Sub-tribe: Epiphyllanae. (4) Genus: Zygocactus. (5) Species: *truncatus* (Haworth) Schumann.

*B. Commercial.*—Thanksgiving-Christmas blooming cactus.

Form: Terrestrial, shade-loving, succulent, leafless plant with jointed and branched stems.

Stems:

*A. General.*—Irregular with usually multi-chotomous branching of upright, adventitiously rootable, flattened cladophylls that have a prominent midrib and prominently toothed lateral wings.

*B. Cladophylls.*—(1) General: Elongated and flat with transversely elongated, areole bearing, truncated apex, with inwardly tapering basal wing margins that merge through a broad usually pointed basal juncture with the cladophyll therebelow, with an axillary areole associated with each tooth, and with some tendency for wings to curl. (2) Midrib: (a) General—Extends longitudinally of cladophyll and continuously through joints with laterally tapering cortex at wing insertions. Pith surrounding vascular bundles that branch and provide lateral extensions of the vascular system to marginal teeth. (b) Texture—Smooth waxy epidermis with wax in small embedded scales and becoming corky in basal stem areas with age. (c) Size (2–6 mos. old)—(1) Length—Usually between 42 and 64 mm. (2) Thickness—Usually between 2.2 and 8.5 mm. (d) Color (at maturity)—Commonly moderate yellow green (near 7.5 GY 5/6) (5 GY 5/6) (5 GY 6/6), dark yellowish green (10 GY 3/4) and/or moderate olive green (7.5 GY 3/4) (near 7.5 GY 4/4). (3) Wings: (a) General shape—Generally flattened from midrib cortex to tooth insertions with prominent lateral thickenings of the vascular system. (b) Margins—Toothed (modified leaves). (c) Texture—Succulent to leathery with smooth waxy epidermis having wax arranged in small embedded scales and becoming corky in basal plant areas with age. (d) Size (2–6 mos. old)—(1) Center thickness—Usually between 1.0 and 2.5 mm. (2) Width (as measured from cladophyll axis to most offset lateral areole)—Usually between 11 and 23 mm. (e) Color (at maturity)—Commonly moderate yellow green (near 5 GY 5/6) and/or moderate olive green (7.5 GY 4/6) (near 5 GY 4/4). (4) Teeth: (a) General shape—Generally flattened and tapered along margins from wing insertions to an apex having a hyaline, single cell, pointed apine with nonpredictable bending, and with irregular adaxial and abaxial marginal curvatures. (b) Orientation—Usually projects generally distally of cladophyll base with the median of the tooth angles (as measured at the distal side of the intersect with the cladophyll axis of a line through the tooth apex and the midpoint between the abaxial and adaxial areoles thereof) formed by non-basal teeth of a cladophyll usually being between 9° and 25°. (c) Margins—Entire. (d) Texture—Succulent to leathery with smooth waxy epidermis having wax in small embedded scales and becoming corky in basal plant areas with age. (e) Number—Usually from 6 to 8 per cladophyll. (f) Size (2–6 mos. old)—(1) Center thickness—Usually between 0.5 and 2.0 mm. (2) Areole to apex dimension (adaxial marginal side)—Usually between 2 and 14 mm. (g) Color (at maturity)—Commonly moderate yellow green (near 5 GY 5/6) and/or moderate olive green (7.5 GY 4/6) (near 5 GY 4/4). (5) Areoles: (a) Terminal areole—Large elongated oval-shaped with several acicular bristles, copious multicellular hairs, and several buds that may mature into either new cladophylls or flowers. The opposite ends of the areole are located adjacent to subsidiary areoles which are in turn located at the axils of teeth that are located at the distal end of cladophyll. (b) Axillary areoles—Acicular bristles without glochidia but having copious, short, brownish to colorless, multicellular hairs. In arsoles that are located below the teeth at the distal end of the cladophyll, there is usually only one bud that is frequently latent.

Buds: Unarmored, ovoid and chlorphyllous.

Flowers:

*A. General.*—Sessile, zygomorphic, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

*B. Sepaloid series.*—(1) General: Free tepals inserted on top of ovary. (2) Shape: Generally tapered from insertion to apex with some deltoid tendencies in outer members of whorl and grading inwardly in the whorl to provide progressively broader apices and longer base-tip dimensions. All members have pointed tip and entire margins with sparse irregular teeth appearing mainly in apex areas of the inner members of the whol. (3) Texture: Succulent and glabrous outer whorl members and grading inwardly in the whorl to silken blades with fleshy basal areas. (4) Number: Usually between 4 and 10. (5) Size (at full bloom): (a) Base-tip dimension—Usually less than 34 mm. (b) Maximum width dimension—Usually less than 15 mm. (6) Color: Varies from the smallest to the largest tepals in outer whorl members with the smallest tepal usually having a continuous field that in color has a yellow green hue while the largest tepal usually has a marginal blade area which in color is dominated by purple and/or purplish pink hues and a basal area which in color is dominated by a yellow green hue. The colors in the marginal and basal areas tending to surround and merge inwardly with a translucent white center field. Commonly light yellow green (2.5 GY 8/6), moderate yellow green (5 GY 7/6), strong yellow green (2.5 GY 7/8) (5 GY 7/8) and/or brilliant yellow green (2.5 GY 8/8) in the continuous field and basal areas and light purple (7.5 P 7/8), pale purplish pink (10 P 8/4) (2.5 RP 8/4) (5 RP 8/4) (7.5 RP 8/4), light purplish pink (5 RP 8/6) and/or moderate purplish pink (10 P 7/6) (10 P 7/8) (2.5 RP 7/6) in marginal areas. The inner whorl members have a translucent white basal area that extends distally in the tepal and merges with a marginal blade area which in color is dominated by reddish purple and/or purplish pink hues. The translucent white basal areas commonly have a greenish cast at the tepal insertion and there is some tendency for the cast to extend distally of the insertion along the tepal axis. Commonly light reddish purple (2.5 RP 6/8), strong reddish purple (near 2.5 RP 5/10), and/or deep purplish pink (near 5 RP 6/10) (near 7.5 RP 6/10) in marginal blade areas. (7) Orientation at full bloom: Varying inwardly in the whorl from erect to recurve.

*C. Tube laminating series.*—(1) General: Inserted on ovary and basally united below the throat as outer laminations on the perianth tube and with progressively greater amounts of basal fusion inwardly in the whorl. (2) Shape: Grading inwardly in whorl with progressively longer base-tip dimensions and progressively broader apices so that blades. (4) Number: Usually 6 to 10. (5) Size (at tulate with acute tips. Entire margins with sparse irregular teeth mainly in apex areas. (3) Texture: Succulent, slightly fleshy, basal areas with silken blades. 4) Number: (Usually 6 to 10. (5) Size (at full bloom): (a) base-tip dimensions—Usually between 32 and 61 mm. (b) Maximum width dimensions—Usually between 12 and 20 mm. (6) Color: Tepals with translucent white basal areas that extend distally in the tepal and merge with marginal blade areas that in color are dominated by purplish pink, purplish red and/or reddish purple hues. Commonly moderate purplish pink (10 RP 7/8) (2.5 RP 7/6), dark purplish pink (5 RP 6/8), deep purplish pink (5 RP 6/10) (7.5 RP 6/10), light reddish purple (10 P 6/8) (2.5 RP 6/8), strong reddish purple (10 P 5/10) and/or moderate purplish red (5 RP 5/10) (7.5 RP 5/10) in marginal areas. (7) Orientation at full full bloom: Recurved.

*D. Tube forming series.*—(1) General: Basally united to form hollow perianth tube that is inserted on ovary and equipped with irregular carina (keel) at throat. (2) Shape: (a) Perianth tube—Elongated with longitudinal floral axis usually at an angle between 30° and 40° with the vertical axis of the ovary and ellipsoidal in cross section with the major ellipsoidal axis arranged generally perpendicular to the general plane of the caldophyll. (b) Blades—Nearly zygomorphic, thin spatulate with acute tip. Entire margins with sparse, irregular teeth mainly in apex area. (c) Carina (keel)—Irregular and transcending. (3) Texture: (a) Perianth tube—Thick, succulent and slightly ribbed. (b) Blades—Translucent and silken. (c) Carina (keel)—Fleshy. (4) Blade number: Usually 8 or 9. (5) Size (at full bloom): (a) Perianth tube—(1) Base to keel length—Usually between 32 and 35 mm. (2) Internal major axis (at throat)—Usually between 8 and 12 mm. when measured perpendicular to axis of perianth tube. (3) Internal minor axis (at throat)—Usually between 6 and 9 mm. when measured perpendicular to axis of perianth tube. (b) Blades—(1) Length (keel to tip)—Usually between 27 and 36 mm. (2) Width (maximum)—Usually between 8 and 14 mm. (6) Color (at full bloom): (a) Perianth tube—A translucent white. (b) Blades—Tepal blades with marginal blade areas which in color are dominated by reddish purple and/or purplish pink hues that merge with a translucent white proximal area located distally of the keel. Commonly strong reddish purple (near 10 P 5/10) (2.5 RP 5/10) and/or deep purplish pink (5 RP 6/10) in marginal areas. (c) Carina (keel)—Commonly strong reddish purple (10 P 5/10) (2.5 RP 5/10) and/or moderate purplish red (near 5 RP 5/10). (7) Orientation at full bloom: Erect to recurve.

*E. Androecium (stamens).*—(1) General: Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. (2) Stamen number: (a) Tube attached group—Usually between 97 and 103. (b) Basally united group—Usually between 19 and 25. (3) Filament: (a) General—Translucent and glabrous with anther connective. (b) Shape—Long, slender and gradually tapering from base to anther connective. (c) Texture—Glabrous and silken. (d) Color—Translucent white at proximal end and commonly light moderate pink (10 P 8/4), moderate pink (10 P 7/6), strong pink (10 P 7/8), pale purplish pink (2.5 RP 8/4) and/or moderate purplish pink (2.5 RP 7/6) (5 RP 7/6) at distal end with colors merging therebetween. (e) Size (at full bloom)—(1) Length—(a) Tube attached group—Usually between 39 and 50 mm. (b) Basally united group—Usually between 39 and 52 mm. (2) Diameter—Usually between 0.2 and 0.3 mm. intermediate the opposite ends. (4) Anthers: (a) General—Adnate with four longitudinally dehiscent pollen sacs. (b) Shape—Elongated. (c) Texture—Waxy. (d) Color (before dehiscing)—Usually pale yellow (5 Y 9/4) and/or pale yellowish green (7.5 Y 9/4). (e) Size—Usually 1.2 to 2.1 mm. in length.

*F. Gynoecium (pistil).*—(1) General: Compound, parietal placentation with united style surrounded by annular diffuse nectary at its insertion. (2) Style: (a) General—Hollow, stout and inserted in ovary. (b) Shape—Elongated, cylindrical and generally tapering. (c) Texture—Fleshy and glabrous with short inner glutinous hairs at distal end. (d) Color—Usually strong reddish purple (near 10 P 5/10) (near 10 RP 4/10). (e) Size (at full bloom)—(1) Length—Usually between 57 and 64 mm. (2) Diameter—Usually varies from about 0.5 to about 1 mm. (3) Stigma: (a) General—Exserted and erect with usually 7 or 8 inner marginally adhering lobes. (b) Shape—Elongated and tapering toward lobe tips and having relatively blunt apices with a tendency toward bifurcation. (c) Texture—Fleshy and smooth with short glutinous hairs. (d) Color—Usually strong reddish purple (2.5 RP 5/10) (10 P 5/10). (e) Size (lobe length at full bloom)—Usually between 3.4 and 5.7 mm. (4) Ovary: (a) General—Epigynous with thin epidermis and distally located concavity and with single cavity having from 6 to 7 carpels with numerous ovules. (b) Shape—Terete to ovoid and generally broadening from insertion to floral end. (c) Texture—Succulent and glabrous with thin outer epidermis. (d) Color—Usually light yellow green (2.5 GY 8/6) (5 GY 8/6), moderate yellow green (2.5 GY 7/6) (5 GY 7/6) (2.5 GY 6/6)

and/or brilliant yellow green (2.5 GY 8/8). (e) Size (at full bloom)—(1) Length (insertion to concavity base)—Usually between 7 and 8 mm. (2) Major axis (distal end of concavity)—Usually between 7 and 11 mm. (3) Minor axis (distal end of concavity)—Usually between 6 and 10 mm.

Growing characteristics: A fast growth rate with the production of more than 1.3 times the number of mature cladophylls during comparable growing periods than either parent, a more upright and compact (denser) appearance than its parents, as evidenced by more erect stems with heavier (more frequent) branching, a greater resistance than its parents to nutrient deficiencies, and a bloom life (from initial tepal separation to initial tepal withering) of from about 6 to about 8 days.

The following is a general description of a specimen of the new plant variety that was grown from the propagation of a single cladophyll in a nursery at Winter Garden, Fla.

Age of plant: 10 months from initial propagation.
Branches from propagated cutting: 3.
Total number of cladophylls grown from cutting: 33.

General:

| Branch No. | No. of cladophylls | Max. length, mm. | No. of tips |
|---|---|---|---|
| 1 | 13 | 233 | 7 |
| 2 | 15 | 297 | 6 |
| 3 | 13 | 186 | 7 |

Midribs:

| Branch No. | Length (avg.), mm. | Thickness (avg.), mm. |
|---|---|---|
| 1 | 58.3 | 4.1 |
| 2 | 59.4 | 4.7 |
| 3 | 46.5 | 4.2 |

Wings:

| Branch No. | Center thickness (avg.), mm. | Max. width (avg.), mm. |
|---|---|---|
| 1 | 1.93 | 17.9 |
| 2 | 2.34 | 20.7 |
| 3 | 1.86 | 14.8 |

Teeth:

| Branch No. | No. of cladophylls (avg.) | Center thickness (avg.), mm. | Areole to apex dimension (avg.), mm. | Tooth angle (median), degrees |
|---|---|---|---|---|
| 1 | 8.0 | 1.87 | 12.1 | 18.6 |
| 2 | 7.8 | 1.03 | 9.6 | 20.1 |
| 3 | 7.9 | .97 | 7.7 | 17.2 |

Cladophyll color: Moderate yellow green (5 GY 5/6), moderate olive green (7.5 GY 4/6).

The following is a general description of a flower of the new plant variety which bloomed in November on a plant grown under shaded glasshouse nursery conditions in Winter Garden, Fla.

Bloom life: 7 days.
Sepaloid series of tepals:
(1) *Number.*—8.
(2) *Size (at full bloom).*—(a) Maximum base-tip dimension—31 mm. (b) Minimum base-tip dimension—3 mm. (c) Maximum width dimension—13 mm.

(3) *Color.*—Strong yellow green (2.5 GY 7/8), brilliant yellow green (2.5 GY 8/8) with marginal blade area of pale purplish pink (10 P 8/4) (2.5 RP 8/4) and (5 RP 8/4), in outer whorl members. Light yellow green (5 GY 9/6) in basal area of inner whorl members and changing to light reddish purple (2.5 RP 6/8), strong reddish purple (2.5 RP 5/10) and deep reddish purple (5 RP 6/10) along the major portion of blade.

Tube laminating series:
(1) *Number.*—8.
(2) *Size (at full bloom).*—(a) Maximum base-tip dimension—60 mm. (b) Minimum base-tip dimension—35 mm. (c) Maximum width dimension—18 mm. (d) Minimum width dimension—14 mm.
(3) *Color.*—Translucent white at base changing distally to light reddish purple (10 P 6/8), strong reddish purple (10 P 5/10), moderate purplish pink (10 P 7/6) (2.5 RP 7/6), dark purplish pink (5 RP 6/8), deep purplish pink (5 RP 6/10), and moderate purplish red (5 RP 5/10) (7.5 RP 5/10).

Tube forming series of tepals:
(1) *Number.*—9.
(2) *Size (at full bloom).*—(a) Perianth tube—(1) Base to keel length—34 mm. (2) Interior major axis (at throat)—10 mm. (3) Interior minor axis (at throat)—8 mm. (b) Blades—(1) Maximum length (keel to tip)—35 mm. (2) Minimum length (keel to tip)—30 mm. (3) Maximum width—13 mm. (4) Minimum width—10 mm.
(3) *Color.*—(a) Perianth tube—A translucent white. (b) Blades—Strong reddish purple (10 P 5/10) (2.5 RP 5/10), moderate purplish red (5 RP 5/10), and deep purplish pink (5 RP 6/10). (c) Carina (keel)—Moderate purplish red (5 RP 5/10) and strong reddish purple (10 P 5/10) (2.5 RP 5/10).

Androecium:
(1) *Stamen number.*—(a) Tube attached group—101. (b) Basally united group—23.
(2) *Filaments.*—(a) Color—A translucent white distal 30% moderate pink (10 P 7/6), strong pink (10 P 7/8) and moderate purplish pink (2.5 RP 7/6). (b) Size (at full bloom)—(1) Length—(a) Tube attached group—47 mm. (avg.). (b) Basally united group—48 mm. (avg.). (2) Diameter—About 0.27 mm. intermediate the opposite ends.
(3) *Anthers.*—(a) Color (before dehiscing)—Pale yellowish green (7.5 Y 9/4). (b) Size—1.9 mm. (avg.).

Gynoecium (pistil):
(1) *Style.*—(a) Color—Strong reddish purple (10 RP 4/10). (b) Size (at full bloom)—(1) Length—62 mm. (2) Diameter—Varies from .5 to 1 mm.
(2) *Stigma.*—(a) Color—Strong reddish purple (10 P 5/10) (2.5 RP 5/10). (b) Size (lobe length)—5 mm.
(3) *Ovary.*—(a) Color—Moderate yellow green (2.5 GY 6/6) (2.5 GY 7/6) (5 GY 7/6). (b) Size (at full bloom)—(1) Length (insertion to concavity base)—7.5 mm. (2) Major axis (distal end of concavity)—9 mm. (3) Minor axis (distal end of concavity)—7.5 mm.

I claim:

1. The new and distinct hybrid plant variety of the Cactaceae family as desribed and illustrated and which is principally distinguished by a growth habit that combines the following characteristics:

1. a faster growth rate than specimens of the "Chrismas Cheer" variety, 2. substantially greater resistance to flower bud abscission than specimens of the "Christmas Cheer" variety,
3. broader, longer and thicker cladophylls than specimens of the "Chirstmas Cheer" variety,
4. a more upright and compact appearance than specimens of the "Christmas Cheer" variety,
5. greater resistance to nutrient deficiencies and fungus-type diseases than specimens of the "Christmas Cheer" variety, and 6. a flower which has a bloom life from about 6 to about 8 days and perianth tube laminating and forming tepals with marginal blade areas that in color are dominated by purplish pink, reddish purple and/or purplish red hues.

References Cited

UNITED STATES PATENTS

P.P. 3,574 6/1974 Cobia ---------- Plants—88

ROBERT E. BAGWILL, Primary Examiner

PO-1050
(5/69)

UNITED STATES PATENT OFFICE
CERTIFICATE OF CORRECTION

Patent No P. 3,290 Dated March 11, 1975

Inventor(s) Barnell L. Cobia

It is certified that error appears in the above-identified patent and that said Letters Patent are hereby corrected as shown below:

Column 4, Line 60 "whol" should read -- whorl --;
Column 5, Lines 32-34 inclusive should read -- blade area changes from ovate inwardly to spactulate with acute tips. Entire margins with sparse irregular teeth mainly in apex areas. (3) Texture:
Line 36 before "Usually" delete the -- ( -- (parenthesis).

Signed and sealed this 10th day of June 1975.

(SEAL)
Attest:

RUTH C. MASON
Attesting Officer

C. MARSHALL DANN
Commissioner of Patents
and Trademarks